(12) United States Patent
Gregoriadis

(10) Patent No.: US 7,381,421 B2
(45) Date of Patent: Jun. 3, 2008

(54) LIPOSOMES

(75) Inventor: Gregory Gregoriadis, London (GB)

(73) Assignee: Lipoxen Technologies Limited, London (GB)

( * ) Notice: Subject to any disclaimer, the term of this patent is extended or adjusted under 35 U.S.C. 154(b) by 86 days.

(21) Appl. No.: 10/149,670

(22) PCT Filed: Dec. 12, 2000

(86) PCT No.: PCT/GB00/04766

§ 371 (c)(1),
(2), (4) Date: Sep. 26, 2002

(87) PCT Pub. No.: WO01/41739

PCT Pub. Date: Jun. 14, 2001

(65) Prior Publication Data

US 2003/0078225 A1    Apr. 24, 2003

(30) Foreign Application Priority Data

Dec. 13, 1999  (EP) .................................. 99310032

(51) Int. Cl.
*A61K 9/127*  (2006.01)
(52) U.S. Cl. ...................... 424/450; 424/812
(58) Field of Classification Search ................ 424/450
See application file for complete search history.

(56) References Cited

U.S. PATENT DOCUMENTS 4,078,052 A * 3/1978 Papahadjopoulos ......... 424/450
4,897,355 A   1/1990 Eppstein et al.
5,756,122 A * 5/1998 Thierry et al. ............... 424/450
6,340,591 B1 * 1/2002 Margolis et al. .......... 435/320.1
2002/0142001 A1 * 10/2002 Brunham ................. 424/184.1

FOREIGN PATENT DOCUMENTS

| EP | 0475178 | 3/1992 |
| GB | 2 164 624 | * 3/1986 |
| WO | WO 9810748 | 3/1993 |
| WO | WO 9740679 | 11/1997 |

OTHER PUBLICATIONS

Walters et al, J. Virol 74, 535-540, 2000.*
Fasbender et al, J. Clin. Invest. 102, 184-193, 1998.*
Gould-Fogerite et al., Muscosal and Systemic Using Cochleate and Liposome Vaccines, J. Liposome Research 6 (2), pp. 357-379, Marcel Dekker, Inc. 1996.
Yang Y-W, et al., "Calcium Phosphate as a Gene Carrier: Electron Microscopy," Biomaterials, 1997, pp. 213-218, vol. 18.

* cited by examiner

*Primary Examiner*—Gollamudi S. Kishore
(74) *Attorney, Agent, or Firm*—Morrison & Foerster LLP

(57) ABSTRACT

Polyanionic therapeutic compounds, generally nucleic acids, are complexed with calcium phosphate and entrapped within liposomes. For DNA vaccines, the complexation and entrapment process provides improved immune response for gene vaccines delivered intramuscularly.

15 Claims, 3 Drawing Sheets

LIPOSOMES

The present invention relates to liposomes containing therapeutic polyanionic compounds, especially nucleic acids. The polyanionic compound is entrapped within the interior space in a form such that improved entrapment efficiency and delivery into cells is achieved.

Gene therapy has been proposed for a variety of indications. In vivo and ex vivo therapy requires that the nucleic acid, usually DNA, get into the cells. Most commonly viruses are used as vectors for gene therapy. It is also known to inject DNA complexed with calcium phosphate directly into the liver or muscles. This causes some cells to take up the DNA and express the genes. However this approach has not been effective for delivery of gene vaccines, that is DNA which encodes for therapeutically interesting antigens.

Considering the polyelectrolyte property of DNA, calcium phosphate can interact with DNA to form complexes (Yang, Y-W. Yan, J-C (1997) Biomat 18, 213-217).

Liposomes have been used as vehicles for genes. For instance in our earlier application WO-A-9810748, we describe entrapment of DNA into the interior space liposomes formed from liposome materials including cationic compounds. The use of cationic liposome forming components improves entrapment efficiency for polyanionically charged therapeutically interesting compounds such as nucleic acids. Our studies on these liposomes have shown that plasmid DNA entrapped in cationic liposomes induces much greater humoral and cell mediated immunity to the encoded antigen than naked DNA in mice immunized by a variety of routes.

Cationic liposomes have been used to deliver DNA for conventional gene therapy, for instance in U.S. Pat. No. 4,897,355. However the DNA is merely complexed on the outside of the liposomes.

In EP-A-0475178 genes are entrapped within the interior space of cationic liposomes.

Cochleates form a category of drug delivery system distinct from liposomes. They consist of solid lipid sheets rolled into a scroll shape. The lipids must include an anionic lipid such as phosphatidyl serine and/or phosphatidyl glycerol. The neighbouring sheets are held together with calcium ions. A description of cochleates and their use in delivery of peptide antigens is disclosed by Gould-Fogerite et al in J. Liposome Res. (1996), 6(2), 357-379. Cochleates have also been proposed for delivery of genes.

Cochleates are formed by forming liposomes including the anionic lipids. The loaded liposomes are then contacted with relatively high concentrations of calcium which results in the formation of long sheets of calcium-chelated phospholipid bilayers. The sheets roll up to form cochleate cylinders which are insoluble precipitates containing substantially no internal aqueous space.

Calcium may be removed from the cochleates, by chelation or dialysis to form large unilamellar vesicles (LUV's). Alternatively cochleates containing active ingredients may be used as such. Active ingredient is incorporated either in the initial liposome forming step, in which case the interior liposome space contains active, or is admixed with pre-formed empty cochleates prior to removal of calcium. LUV's may be useful as the drug delivery system. Gould-Fogerile et al believe that contact of the cochleate with a cell results in a fusion event and delivery of encochleated material to the interior of a target cell.

There are provided in the present invention novel liposomes formed of liposome forming components and, entrapped within the interior space, a complex of a therapeutic polyanionic compound having a molecular weight of at least 1000 D and calcium phosphate.

Although the liposome forming components may contain some compounds which are negatively charged at neutral pH, preferably such quantities are low, or the liposome forming components are free of such compounds.

Although the liposome forming components may contain compounds which are cationically charged at neutral pH, it is generally preferred that such compounds are present at low levels, for instance less than 20 mol % of total liposome forming components, or that the liposome forming components are substantially free of such compounds. It is generally desirable to minimise the administration of cationic liposomes since these may have an adverse effect in certain circumstances.

The polyanionic compound of therapeutic interest should generally have at least three anionic charges per molecule (under conditions of neutral pH, and should have a molecular weight of at least 1000 D). Preferably the compound is oligomeric or polymeric, and is most preferably a polypeptide, protein or nucleic acid. The invention is of most utility in delivery of RNA or, most preferably DNA. The invention is particularly useful for delivering gene vaccines, that is DNA or RNA operatively encoding an antigenic peptide or protein. Preferably a gene vaccine comprises double stranded DNA. The DNA may be linear or circular.

In the invention, the ratio of calcium phosphate to nucleic acid should be optimised so as to ensure full complexation of nucleic acid, without requiring excess of calcium, or inadequate calcium for full recover of nucleic acid as complex. Preferably the ratio of calcium ions (based on $Ca^{2+}$):DNA is in the range 1 mole:(1-4 g). For polyanionic compounds other than DNA, the ratio should be adapted depending on the level of anionic charges in the molecule (equivalents per weight basis). The same (mole:wt) ratios are appropriate for RNA as for DNA.

The liposome forming components, preferably have substantially no overall charge at neutral pH. Particularly suitable components are phospholipids, especially phosphatidyl cholines optionally in combination with phosphatidyl ethanolamines. The fatty acyl components of the phospholipids are generally selected according to the level of fluidity of the liposome membrane required. Particularly suitable phospholipids include lecithin, for instance from eggs or soya bean.

Preferably the liposome forming components include cholesterol, which provides increased stability. Preferred liposomes include up to 50% by mole cholesterol based on total liposome forming components.

In a preferred composition of liposome forming components, phosphatidyl choline is present in an amount in the range 10 to 90% by mole, more preferably in the range 40 to 75% by mole.

The liposomes of the invention preferably also contain within the interior space one or more sugars, preferably a mono- or di-saccharide.

Suitable sugars include sucrose and glucose. The presence of such components enables liposomes of smaller size, and more controllable size, to be formed.

The lipsomes of the present invention preferably have an average diameter in the range 100 nM to 5 μm, more preferably in the range 200 nM to 1 μm. Liposomes at the lower end of the range are generally preferred for delivery of therapeutic polyanionic compounds which are peptide therapeutics, peptide antigens, or conventional gene therapy. For gene vaccines, the size of the liposomes may be at the lower or higher end of the range.

According to a further aspect of the invention there is provided a method of forming liposomes containing a therapeutic polyanionic compound, in which empty liposomes (that is liposomes which do not contain the therapeutic polyanionic compound, either in the interior space, or complexed with the outer surface), formed of liposome forming components, are mixed with a complex of the polyanionic compound and calcium phosphate in aqueous suspension, the aqueous mixture is dehydrated, and the dried mixture is rehydrated in aqueous rehydration medium to form liposomes which are dehydration/rehydration vesicles (DRV's) in which the complex is entrapped in the interior space.

In the method of the invention, the liposome forming components, the polyanionic compounds and the ratios of calcium to polyanionic compound are preferably as defined for the novel liposomes above.

In the method, there is generally provided a preliminary complex formation step, in which an aqueous phosphate salt solution is mixed with an aqueous calcium salt solution, one other calcium and phosphate solutions further containing dissolved or suspended therein the therapeutic polyanionic compound, whereby a flocculated complex of polyanionic compound in calcium phosphate is formed. The phosphate salt solution is formed from a suitable water-soluble inorganic salt of phosphate, generally sodium or potassium phosphate. Often the phosphate salt solution contains other salts, for instance sodium chloride. It is often convenient to use convention phosphate buffered saline, or HEPES. Such buffers contain dissolved phosphate ions at a concentration (based on $PO_4^{3-}$) in the range 0.5 to 500 mM.

The calcium salt solution should be formed from a suitable water-soluble inorganic or organic salt of calcium. Calcium chloride is readily available and is suitable.

The polyanionic compound may be dissolved in either one of the calcium or phosphate solutions. It is found to be convenient to premix the polyanionic compound with the calcium salt solution, since this allows optimum control of the ratio of calcium to polyanionic compound. The phosphate solution may then be added to the calcium/polyanionic solution until flocculation appears to be optimised (i.e. there is no further floc formed).

By the method of the invention it has been shown that the flocculated complex may contain up to 100%, for instance at least 80%, more preferably at least 90%, of the polyanionic compound. Preferably the flocculated complex is washed before being mixed with the empty liposomes, for instance using water, saline solution or, preferably, a phosphate buffered saline.

In the method, it may be convenient to include dissolved sugar in the step of mixing empty liposomes with the complex. This results in sugar being incorporated with the complex into the interior space of the liposomes. The incorporation of sugar at this stage results in the DRV's having a reduced, and more controlled average diameter, whilst retaining the high entrapment ratios for the complex. Suitable sugars are as described above in connection with the novel liposomes.

It may be desirable to subject the DRV's to a microfluidisation step. Such a step is desirable if no sugar is included to provide optimum control of the liposome size.

The final product liposomes preferably have a size in the range 100 nM to 500 μm, most preferably in the range 200 nM to 1 μm.

It may be desirable for the liposome suspension to be washed before further use. For instance by washing the liposomes with an acidic aqueous washing solution, non-entrapped complex should be removed from the outer surface of the liposomes. The acidic wash solution is believed to dissolve calcium phosphate, thereby disrupting the complex and allowing dissolution of non-entrapped polyanionic compound. A washing step may involve spinning down liposomes from the aqueous suspension in which they have been formed, re-suspending them in aqueous acidic wash liquor and mixing them, followed by spinning the liposomes down and re-suspending them, if desired. These steps may be repeated several times.

In the method of the invention it has been found possible to show entrapment ratios of at least 80% (based on starting polyanionic compound, or polyanionic compound in the complex).

The liposomes may be subjected to further recovery steps, for instance to provide storage-stable dried compositions. Drying steps may include freeze-drying. It is generally found, however, that the aqueous suspension of liposomes is adequately stable to allow storage in that form for appropriate periods of time prior to incorporation in a pharmaceutical composition, or administration to a human or animal.

There is also provided in the invention a liquid composition containing the novel liposome suspended in a continuous aqueous vehicle. Preferably the composition is a pharmaceutical composition and the continuous aqueous vehicle is pharmaceutically acceptable for administration to a human or animal. The composition may contain other pharmaceutically acceptable excipients. Generally the pharmaceutical composition is suitable for injection, for instance intravenous, intraperitoneal, intramuscular or subcutaneous. Alternatively, the novel liposomes may be incorporated into a pharmaceutical composition suitable for inhaling. In such compositions, for instance, the liposomes may be used in substantially dry (free of continuous aqueous phase) form, suspended in a pharmaceutically acceptable gaseous phase. Such compositions may contain other pharmaceutically acceptable excipients known to be suitable for such compositions.

Alternatively the compositions may be suitable for oral delivery. Such compositions generally comprise liposomes suspended in a continuous aqueous phase.

The present invention is illustrated in the following examples. The results of some of the examples are shown in the figures, as follows.

EXAMPLES

In the present invention we first provide flocculated complexes of calcium phosphate and DNA and, subsequently, entrap the complex into liposomes. We present data on the characteristics of the products, which we have named "capisomes" ((Callcium) P(hosphate) isomers).

The DNA is a hepatitis B surface antigen (HBsAg)-encoding plasmid. We investigate the immune responses in Balb/C mice injected intramuscularly with such liposomes.

Example 1

Complex formation 10-100 μg of $^{35}$S-labelled plasmid DNA expressing the hepatitis B surface antigen (S region, plasmid pRc/CMV-HBS of the ayw type was mixed with 10 μl of calcium chloride (2.5M), and this mixture was added into 100 μl of hepes buffer saline (HBS) (pH 7.0) thereby forming 25 μmole calcium phosphate, flocculated by the anionic polyelectrolyte DNA. Then, the suspension ("floc") of calcium phosphate-DNA complexes in HBS were spun down at 735 g (2500 rpm) for 15 minutes, and washed with distilled water twice.

The washed complex was investigated to determine the level of recovery of DNA.

Figure 1:
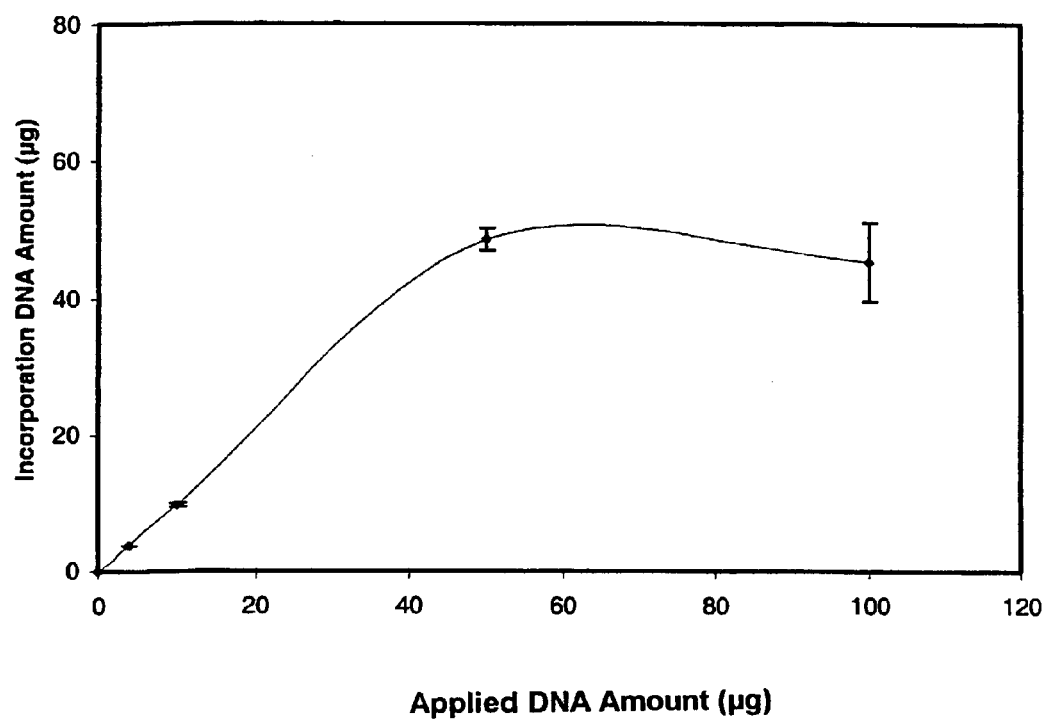
FIG. 1 shows the level of DNA recovered in flocculated complex as described in the method of example 1.

FIG. 1 shows the loading of plasmid pRc/CMV-HBs(S) DNA in the calcium phosphate-DNA complexes. The various amounts of plasmid pRc/CMV-HBs(S) DNA were formed the complexes with 25 μmole calcium phosphate, and the incorporation DNA amounts were evaluated by $S^{35}$-labelled DNA (Data are shown with mean±SD, n=5).

Example 2

The calcium phosphate precipitate of Example 1 was resuspended at 100 μl of distilled water for the entrapments into liposomes by dehydration-rehydration method (Kirby, C et al (1984) Biotechnology 2, 979-984). The calcium phosphate-DNA complexes or naked DNA, for comparison, were resuspended in empty small unilamellar vesicles (SUV) suspension and freeze-dried. (The liposome forming components and amounts are detailed in table 1 and the amount of DNA or complex) The dry powder was dissolved in 1 ml distilled water, and washed by phosphate buffered saline (PBS) twice. The final product was resuspended in PBS. The liposomes were tested for their size and entrapment efficiency (of DNA) by determining the table 35$_S$, The results are shown in Table 1

Similar liposomes made by labelling the DNA with ethidium bromide before complexation and coentrapping the complex with carboxyfluorescein, were also observed under transmission electron microscope, before and after acid wash using acidic wash having pH less than 4. The acid wash can be seen to remove DNA complex from the outside of the liposomes, judging by the difference in size of liposomes as imaged by ethidium bromide (which is assumed to remain with DNA) and carboxyfluorescein (CF) which is assumed to be wholly inside the liposomes, any external CF having been removed at earlier stages in the liposome preparation.

Example 3

Male Balb/C mice, 6-8 weeks old were given 5 intramuscular injections of 10 μg (per injection) naked, PC/Chol (2:2 μmoles), PC/DOPE (2:1 μmoles) and PC/DOPE/DC-Chol (2:1:0.5 μmoles) liposomes entrapped CaPi-DNA complexes or PC/DOPE/DC-Chol (2:1:0.5 μmoles) entrapped plasmid DNA (produced according to the technique described in Example 2) at one week intervals. The mice were bled at different time intervals and rthe sera were tested for anti-HBsAg IgG titre by horseradish peroxidase enzyme-linked immunoadsorbent assay (ELISA) Davis, D. et al (1987) Immunology Lett. 14, 341-348)

Figure 2:
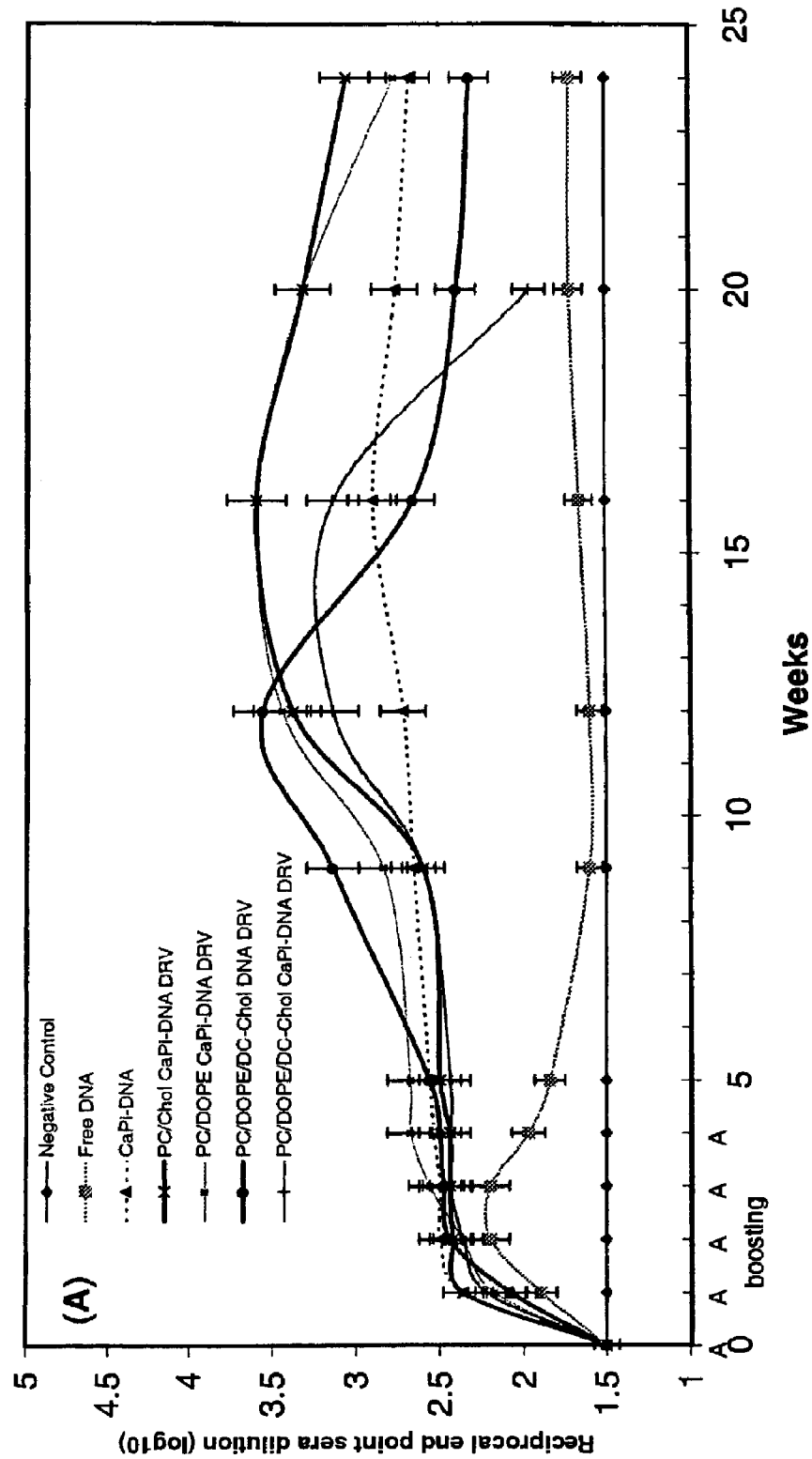
FIG. 2 shows the total IgG responses of mice immunised according to example 3.

The results are shown in FIG. 2 which shows the total IgG responses in mice immunized with naked, or liposome-entrapped pRc/CMV HBS DNA. Balb/c mice were injected intramuscularly on weeks 0, 1, 2, 3, 4 with 10 μg of naked DNA or DNA entrapped in liposomes. Animals were bled at 1, 2, 3, 4, 5, 9, 12, 16, 20 and 24 weeks after the first injection and sera were tested by ELISA for IgG responses against the encoded HBsAg. The values in IgG responses are $\log_{10}$ of reciprocal end point serum dilutions required for OD (the absorbance region) to reach readings of about 0.2 (Data are means±SD, n=5).

Example 4

Figure 3:
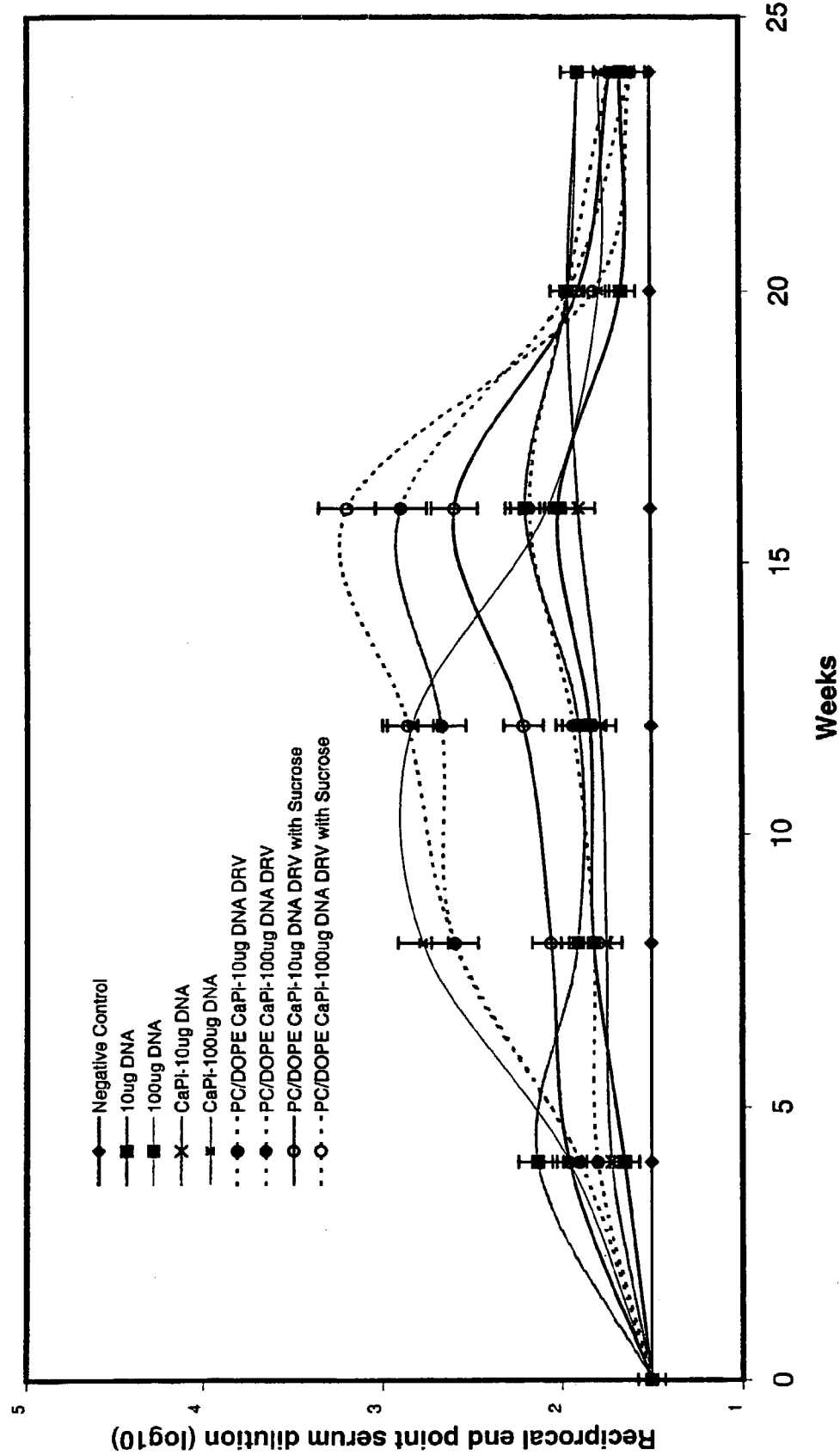
FIG. 3 shows the total IgG responses of mice immunised according to the technique described in example 4.

In another immunisation experiment on the same breed of mice and the same plasmid DNA, a single i.m. injection of 10 lug or 100 μg naked, complexed and entrapped complexed DNA, and complexed DNA coentrapped with sucrose was made and the mice bled at 4, 8, 12, 16, 20 and 24 weeks after the injection. The sera were tested as in Example 3 for total IgG and the results are shown in FIG. 3.

TABLE 1

The characteristics of plasmid DNA-containing capisomes

| DRV Composition | DNA Form | Entrapment Efficiency (%) | Z-Average of Vesicle Size (μm) | Zeta Potential (mV) |
| --- | --- | --- | --- | --- |
| PC/Chol (16:16 μmoles) | 100 μg DNA | 37.62 ± 7.63** | 5.57 ± 2.31** | −26.8 ± 1.6** |
| PC/Chol (16:16 μmoles) | CaPi-100 μg DNA | 81.03 ± 3.19 | 3.50 ± 1.35 | −37.9 ± 0.2 |
| PC/DOPE (16:8 μmoles) | 100 μg DNA | 51.07 ± 5.95** | 24.91 ± 3.84** | −4.3 ± 0.5** |
| PC/DOPE (16:8 μmoles) | CaPi-100 μg DNA | 88.44 ± 2.59 | 8.15 ± 2.78 | −7.7 ± 0.3 |
| PC/DOPE DC-Chol (16:8:4 μmoles) | 100 μg DNA | 92.12 ± 3.89 | 2.51 ± 1.24 | 35.6 ± 0.7 |
| PC/DOPE/DC-Chol (16:8:4 μmoles) | CaPi-100 μg DNA | 89.47 ± 3.12 | 2.79 ± 1.31 | 33.4 ± 1.2 |

(Data are shown with mean ± SD, n = 3, compared with capisome: **p < 0.005)

The results show that the calcium phosphate complexes, when entrapped within liposomes, especially when co-entrapped with sugar, have a greater and longer lasting effect on IgG levels, than naked DNA and/or calcium phosphate complexed DNA and/or entrapped non-complexed DNA at the same levels, for both immunisation regimens. The results show that the "capisomes" are a promising adjuvant for DNA vaccines.

The invention claimed is:

1. A method of inducing an immune response in a human or animal body, which method comprises
    administering to said body a composition of liposomes formed of liposome forming components which consist of compounds having no overall charge,
    wherein said liposomes have entrapped within the interior space, a complex of a nucleic acid compound having a molecular weight of at least 1000 D and calcium phosphate, wherein the ratio of calcium phosphate to nucleic acid is in the range 1 mole $Ca^{2+}$:(1-4)g nucleic acid,
    and wherein the nucleic acid compound is DNA operatively encoding antigen.

2. The method according to claim 1 in which the liposome forming components include cholesterol.

3. The method according to claim 1 in which the liposome forming components include cholesterol.

4. The method according to claim 1 in which the liposome forming components include one or more phosphatidyl cholines, optionally in combination with phosphatidyl ethanolamine.

5. The method according to claim 1 in which the interior space includes also a sugar.

6. The method according to claim 5 in which the sugar is a mono- or di-saccharide.

7. The method according to claim 1 in which the liposomes have an average diameter in the range 100 nm-5 µm.

8. The method according to claim 7 in which the liposomes have an average diameter in the range 200 nm-1 µm.

9. The method according to claim 1 in which the liposomes are in combination with a pharmaceutical acceptable excipient.

10. The method according to claim 1 suspended in a continuous aqueous vehicle.

11. A method of inducing an IgG immune response in a human or animal body wherein said method comprises
    administering to said body a composition of liposomes formed of liposome forming components which consist of compounds having no overall charge,
    wherein said liposomes have entrapped within the interior space, a complex of a nucleic acid compound having a molecular weight of at least 1000 D and calcium phosphate, wherein the ratio of calcium phosphate to nucleic acid is in the range 1 mole $Ca^{2+}$:(1-4)g nucleic acid, and
    wherein the nucleic acid compound is DNA operatively encoding antigen.

12. The method according to claim 11 wherein the antigen is a peptide antigen and in which the composition is administered intramuscularly.

13. The method according to claim 11 wherein liposome forming components include one or more phosphatidyl cholines, optionally in combination with phosphatidyl ethanolamine.

14. The method according to claim 11 wherein the interior space includes a mono- or di-saccharide.

15. The method according to claim 11 wherein the liposomes have an average diameter in the range 100 nm-5 µm.

* * * * *